United States Patent
Jang et al.

(10) Patent No.: US 8,160,691 B2
(45) Date of Patent: Apr. 17, 2012

(54) APPARATUS TO MEASURE SKIN MOISTURE CONTENT AND METHOD OF OPERATING THE SAME

(75) Inventors: Woo Young Jang, Seoul (KR); Jeong Je Park, Daegu (KR); Jae Chan Park, Yongin-si (KR); Hong Sig Kim, Seongnam-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 589 days.

(21) Appl. No.: 11/822,406

(22) Filed: Jul. 5, 2007

(65) Prior Publication Data

US 2008/0012582 A1    Jan. 17, 2008

(30) Foreign Application Priority Data

Jul. 5, 2006 (KR) .................. 10-2006-0063160

(51) Int. Cl.
*A61B 5/05* (2006.01)
(52) U.S. Cl. ........................ 600/547; 600/310
(58) Field of Classification Search .................. 600/547
See application file for complete search history.

(56) References Cited

U.S. PATENT DOCUMENTS

| | | |
|---|---|---|
| 5,738,107 A | 4/1998 | Martinsen et al. |
| 5,947,910 A | 9/1999 | Zimmet |
| 2003/0222662 A1 | 12/2003 | Geisel |
| 2004/0171962 A1 | 9/2004 | Leveque et al. |
| 2005/0159655 A1 | 7/2005 | Kao |
| 2007/0185392 A1* | 8/2007 | Sherman et al. .............. 600/306 |
| 2007/0190006 A1* | 8/2007 | Sherman et al. .............. 424/70.1 |

FOREIGN PATENT DOCUMENTS

| | | |
|---|---|---|
| EP | 1 338 263 A2 | 8/2003 |
| JP | 09-075316 | 3/1997 |
| KR | 10-2001-0067927 | 7/2001 |
| KR | 10-2002-0018254 | 3/2002 |
| KR | 10-2005-0118876 | 12/2005 |
| KR | 10-0634544 | 10/2006 |
| WO | 96/10951 | 4/1996 |
| WO | 2005/018432 A2 | 3/2005 |
| WO | 2005/018432 A3 | 3/2005 |
| WO | 2007/026340 A3 | 3/2007 |
| WO | WO 2007/026430 * | 3/2007 |

OTHER PUBLICATIONS

European Search Report issued Oct. 26, 2007 in corresponding European Patent Application No. 07111725.3-1265.
Marie Loden, "Dry Skin and Moisturizers: Chemistry and Function." Dermatology: Clinical & Basic Science, Second Edition, CRC Press (2005): pp. 452-453.

(Continued)

*Primary Examiner* — Max Hindenburg
*Assistant Examiner* — Renee Danega
(74) *Attorney, Agent, or Firm* — Staas & Halsey LLP (57) ABSTRACT

A method of measuring skin moisture content, the method including: measuring a differential rate of a skin impedance of a predetermined skin area of a user for a predetermined period of time; and determining that the skin area is a moist area when the differential rate of skin impedance is greater than or equal to a predetermined value for a predetermined period of time, and determining that the skin area is a dry area when the differential rate of skin impedance is less than the predetermined value for the predetermined period of time.

4 Claims, 9 Drawing Sheets

OTHER PUBLICATIONS

N. Sekiguchi et al., "Microsensor for the measurement of water content in the human skin." Sensors and Actuators B 78 (2001): pp. 326-330.

O.G. Martinsen et al., "Measurement of the effect of topical liposome preparations by low frequency electrical susceptance." Innov. Techn. Biol. Med., vol. 17, No. 3 (1996): pp. 217-222.

Y. Yamamoto et al., "The measurement principle for evaluating the performance of drugs and cosmetics by skin impedance." Med. & Biol. Eng. & Comput., vol. 16 (1978): pp. 623-632.

K. Cole et al., "Dispersion and Absorption in Dielectrics." J. Chem. Phys., vol. 9 (Apr. 1941): pp. 341-351.

European Office Action issued on May 12, 2009 in corresponding European Patent Application 07111725.3.

* cited by examiner

| SKIN MOISTURE CONTENT INFORMATION \ SKIN AREA | MOIST AREA | DRY AREA |
|---|---|---|
| VERY DRY | < 30 AU | < 15 AU |
| DRY | 30 ~ 49 AU | 15 ~ 29 AU |
| MOIST | 50 ~ 59 AU | 30 ~ 39 AU |
| VERY MOIST | > 60 AU | > 40 AU |

AU : ARBITRARY UNIT

APPARATUS TO MEASURE SKIN MOISTURE CONTENT AND METHOD OF OPERATING THE SAME

CROSS-REFERENCE TO RELATED APPLICATIONS

This application claims the benefit of Korean Patent Application No. 10-2006-0063160, filed on Jul. 5, 2006, in the Korean Intellectual Property Office, the disclosure of which is incorporated herein by reference.

BACKGROUND

1. Field

The present invention relates to an apparatus to measure skin moisture content and a method of operating the same, and more particularly, to an apparatus to measure skin moisture content and a method of operating the same, when measuring skin impedance to determine skin moisture content. A measured skin area is determined to be a moist area when a differential rate of the skin impedance value is greater than or equal to a predetermined threshold for a predetermined period of time, and the measured skin area is determined to be a dry area when the differential rate of the skin impedance value is less than the predetermined threshold for the predetermined period of time.

2. Description of the Related Art

As more and more people become interested in beauty, an interest in skin care has also increased. A desire for healthy skin effects not only beauty-related businesses, but also effects the growth of medical-related businesses as well since people need to protect their skin from ultraviolet rays that have become stronger due to the destruction of the ozone layer, and various types of pollution.

Skin is an organ of the integumentary system made up of multiple layers of epithelial tissues. Main functions of the skin are to protect against pathogens, waterproofing, temperature regulation, insulation, etc. One of the most critical elements to enable the proper performance of the functions of skin is moisture content in a stratum corneum. The moisture content in the stratum corneum is generally called skin moisture content. Maintaining a particular moisture content in the stratum corneum enables the performing of basic functions of skin, such as protecting against harmful substances like pathogens, and preventing excessive evaporation of skin moisture.

In view of skin care, the skin moisture content is also considered an essential element. Accordingly, fundamental to skin care is skin moisture management.

According to a conventional art, an electrical measurement method, an optical measurement method, and a method using a magnetic resonance imaging (MRI) are included in a method of measuring skin moisture content. The electrical measurement method is widely used. More particularly, a method of measuring the skin moisture content by measuring susceptance, i.e. an alternating current (AC) component of admittance, of three electrodes using a sinusoidal wave of 50 KHz is mainly used.

Generally, skin moisture content for each anatomical area is different. Accordingly, when the skin moisture content is a standard for determining whether skin is moist or dry, the skin moisture content may be variously set according to each of the anatomical areas. Thus, the skin moisture content may be measured when a distribution of a value of the skin moisture content is ascertained. In the conventional art, in order to measure the skin moisture content for each of the anatomical areas, the skin moisture content is measured based on different standards after classifying a skin of a user into a moist area and a dry area for convenience.

However, when adopting an apparatus to measure skin moisture content according to the conventional art for a mobile communication terminal, a user is required to input each skin area to be measured, and measure skin moisture content for each of the inputted skin areas, respectively. Accordingly, the method of measuring skin moisture content according to the conventional art may not provide users a convenient measurement of skin moisture content.

Thus, a method of measuring skin moisture content which may automatically classify a skin of a user into a moist area and a dry area, and accurately measure the skin moisture content based on a suitable standard is needed.

SUMMARY

An aspect of the present invention provides an apparatus to measure skin moisture content and a method of operating the same, the apparatus measuring a differential rate of skin impedance of a predetermined skin area of a user for a predetermined period of time, determining whether the skin area of the user is a moist area or a dry area, and may more easily measure the skin moisture content without separately inputting information of the skin area or referring to a particular table.

An aspect of the present invention also provides an apparatus to measure skin moisture content and a method of operating the same, whereby a user initially measures a skin moisture content through the apparatus to measure the skin moisture content, which performs a calibration procedure considering a differential rate of a skin impedance which is measured in a moist area for a predetermined period of time, determines whether a measurement mode is an automatic mode or a manual mode of measuring the skin impedance, and thereby may optimally measure the skin moisture content according to a skin characteristic of the user.

Additional aspects and/or advantages will be set forth in part in the description which follows and, in part, will be apparent from the description, or may be learned by practice of the invention.

The foregoing and/or other aspects are achieved by providing a method of measuring skin moisture content, the method including: measuring a differential rate of skin impedance of a predetermined skin area of a user for a predetermined period of time; and determining that the skin area is a moist area when the differential rate of skin impedance is greater than or equal to a predetermined value for a predetermined period of time, and determining that the skin area is a dry area when the differential rate of skin impedance is less than the predetermined value for the predetermined period of time.

The foregoing and/or other aspects are achieved by providing an apparatus to measure skin moisture content, the apparatus including a measurement module measuring skin impedance of a predetermined skin area of a user; a differential rate calculation module measuring a differential rate of skin impedance of the predetermined skin area for a predetermined period of time; a skin state determination module determining that the skin area is a moist area when the differential rate is greater than or equal to a predetermined value for a predetermined period of time and determining that the skin area is a dry area when the differential rate is less than the predetermined value for the predetermined period of time; and an output device providing skin moisture content information corresponding to the skin area being the moist area or the dry area to the user.

The foregoing and/or other aspects are achieved by providing a method of measuring skin moisture content, the method including measuring a differential rate of skin impedance for a predetermined period of time, with respect to at least a moist area and a dry area of skin areas of a user; determining whether the differential rate of skin impedance is included in a predetermined pattern range; and setting a measurement mode as an automatic mode, when the differential rate is included in the predetermined pattern range, and setting the measurement mode as a manual mode, when the differential rate is not included in the predetermined pattern range.

BRIEF DESCRIPTION OF THE DRAWINGS

The above and/or other aspects and advantages will become apparent and more readily appreciated from the following detailed description, taken in conjunction with the accompanying drawings of which.

DETAILED DESCRIPTION OF THE EMBODIMENTS

Reference will now be made in detail to the embodiments, examples of which are illustrated in the accompanying drawings, wherein like reference numerals refer to the like elements throughout. The embodiments are described below in order to explain the present invention by referring to the figures.

An apparatus to measure skin moisture content according to an embodiment may be embodied as any portable device, e.g. a mobile communication terminal, a personal digital assistance (PDA), a portable game device, an Moving Picture Experts Group Audio-Layer 3 (MP3) player, a portable multimedia player (PMP), a Digital Multimedia Broadcasting (DMB) terminal, a notebook, etc. Specifically, the apparatus to measure skin moisture content may be embodied as a partial configuration of the portable devices or may be independently embodied as a single product, instead of being embodied as the partial configuration of the portable device.

Hereinafter, embodiments of the present invention will be described in detail by referring to the figures.

Figure 1:
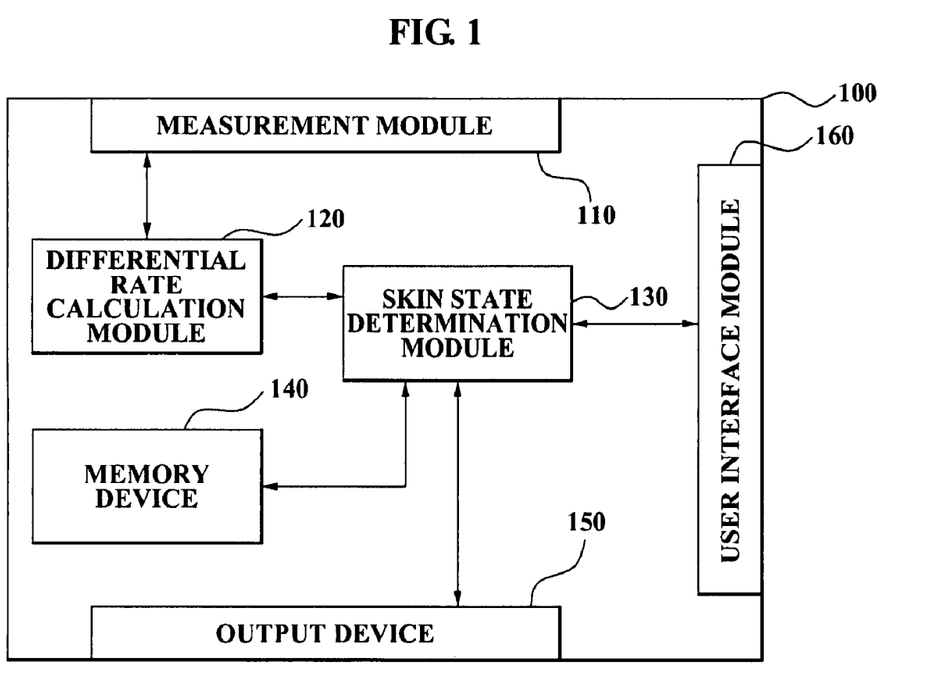
FIG. 1 is a diagram illustrating a configuration of an apparatus to measure skin moisture content according to an embodiment of the present invention.

FIG. 1 is a diagram illustrating a configuration of an apparatus to measure skin moisture content according to an embodiment of the present invention.

The apparatus to measure skin moisture content 100 according to an embodiment includes a measurement module 110, a differential rate calculation module 120, a skin state determination module 130, a memory device 140, an output device 150, and a user interface module 160.

The measurement module 110 measures skin impedance of a predetermined skin area of a user. For this, the measurement module 110 includes a sensor measuring skin impedance including a reference (R) electrode, a current (C) electrode, and a measuring (M) electrode.

Also, the measurement module 110 may be embodied including various types of sensors measuring skin impedance as well as the above-described sensor measuring skin impedance. A measurement operation of measuring skin impedance through the measurement module 110 will be described in detail by referring to FIGS. 2 through 4.

Figure 2:
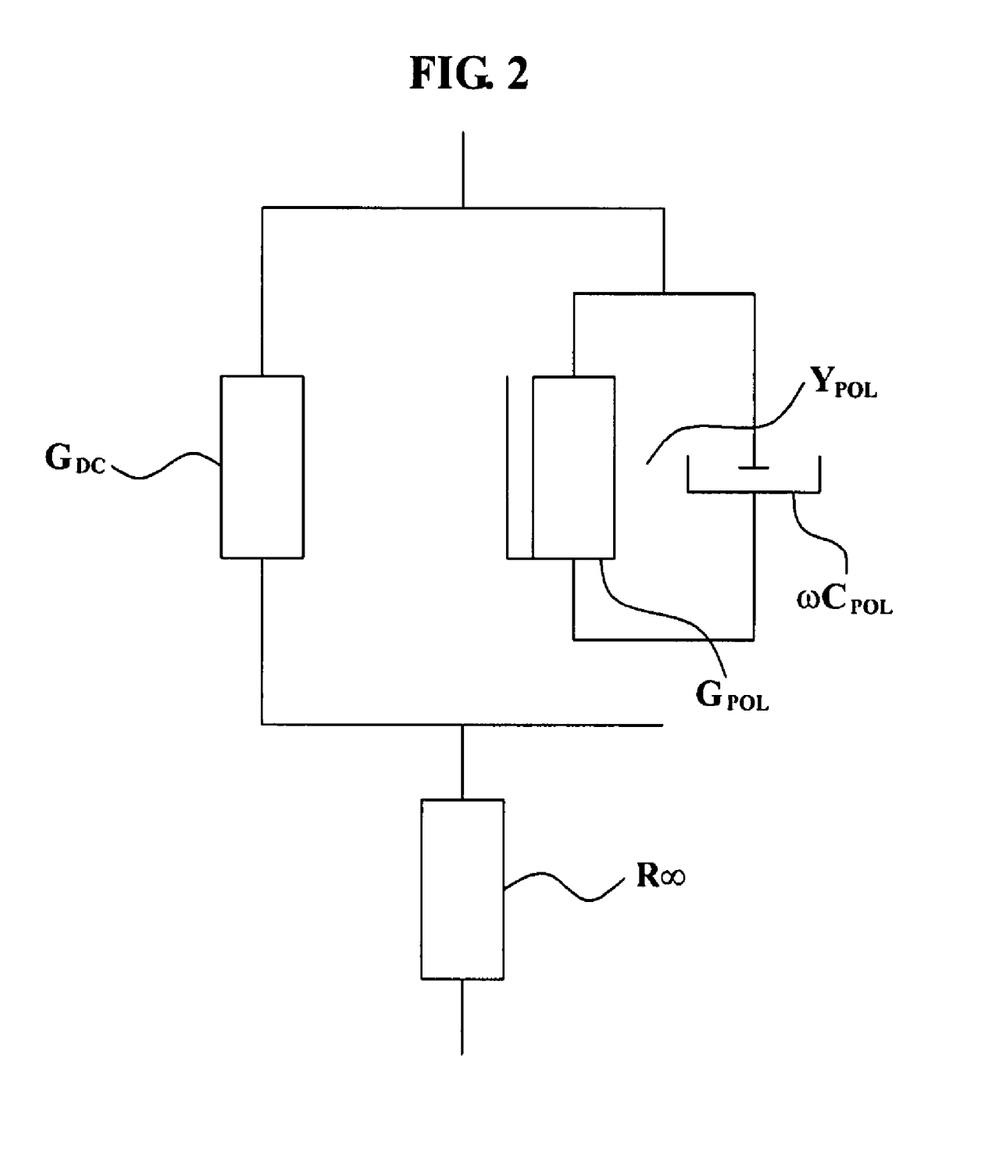
FIG. 2 a diagram illustrating an electrically modeled biological structure of skin according to an embodiment of the present invention.

FIG. 2 a diagram illustrating an electrically modeled biological structure of skin according to an embodiment of the present invention.

Figure 3:
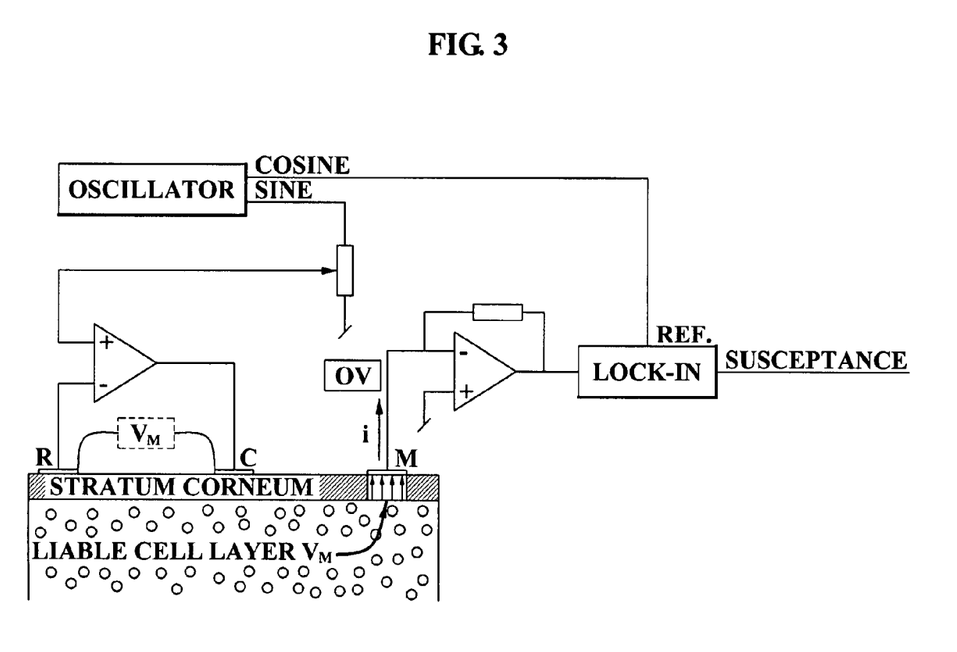
FIG. 3 a diagram illustrating a measurement principle of measuring skin moisture content according to an embodiment of the present invention.

FIG. 3 a diagram illustrating a measurement principle of measuring skin moisture content according to an embodiment of the present invention.

Figure 4:
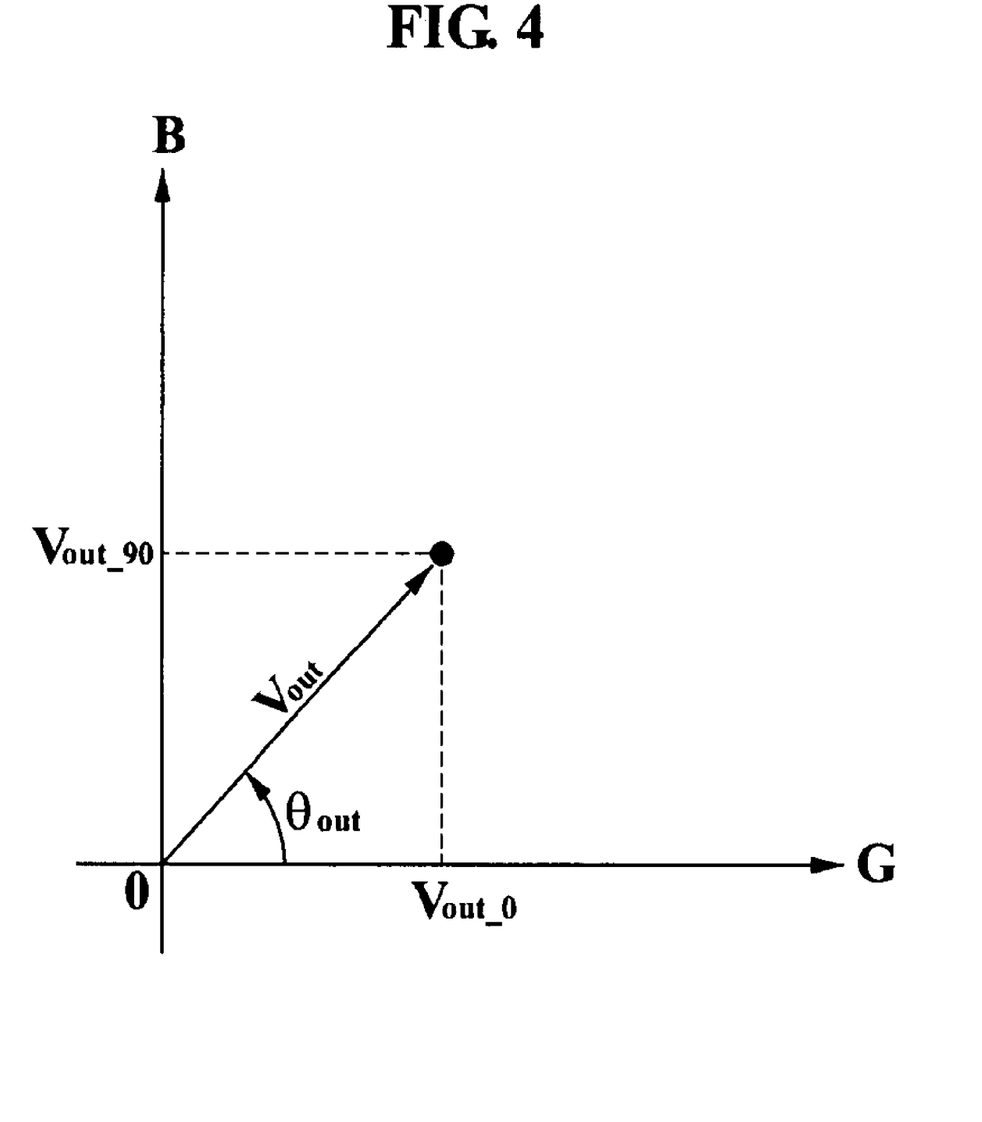
FIG. 4 is a diagram illustrating a graph of an admittance of a skin moisture content measurement according to an embodiment of the present invention.

FIG. 4 is a diagram illustrating a graph of an admittance of a skin moisture content measurement according to an embodiment of the present invention.

To electrically measure the skin moisture content, the biological structure of the skin is required to be electrically modeled. FIG. 2 illustrates an electrically modeled biological structure of a skin by using a Yamamoto-Yamamoto model, 'The measurement principle for evaluating the performance of drugs and cosmetics by skin impedance' in Med. & Biol. Eng. & Comput. 1978. The Yamamoto-Yamamoto model reinterpreted a Cole-Cole model, 'Dispersion and absorption in dielectrics', in J. Soc. Cosmet. Chem. 1941.

In FIG. 2, $G_{DC}$ indicates a sweat gland activity of a stratum corneum. $R_\infty$ indicates a liable cell from a bottom of a stratum corneum to a dermis, which is electrically modeled. The $R_\infty$ is direct current (DC) dominant. $G_{POL}$ indicates an conductance component due to a polarizing phenomenon. $Y_{POL}$ indicates an admittance component due to a polarizing phenomenon, and is alternating current (AC) dominant. A $\omega C_{POL}$ is known to model the skin moisture content of the stratum corneum. Accordingly, when measuring the skin moisture content of the stratum corneum, removing an effect of the $R_\infty$ and the $G_{DC}$ is critical.

To measure only the $\omega C_{POL}$, only susceptance which is an AC component of the admittance component is required to be measured. For this, an analog lock-in amplifier may be utilized. In FIG. 3, an oscillator oscillates a reference signal (cosine wave) to a lock-in amplifier. An R electrode indicates a reference electrode, a C electrode indicates a current electrode, and an M electrode indicates a measuring electrode. $V_m$ is an applied voltage which is applied to the R electrode and the C electrode.

Specifically, the $R_\infty$ may be assumed to be a conductor as shown in FIG. 3. When a constant voltage signal of a regular frequency with respect to a human body is confirmed by using the $R_\infty$ as the conductor, a current may be measured through the conductor of a liable cell layer. In this instance, the regular frequency is $\omega = 2\pi f$, and the current corresponds to an impedance of the stratum corneum. Also, the stratum corneum closely attaches to a measurement electrode. The admittance of the stratum corneum of a measured area may be measured by using the current.

'Vsig=|Vsig|sin(ωrt+θsig)' is a response signal which converts the measured current to a voltage, and 'V$_{L\_90}$=|V$_{L\_90}$|cos(ω$_{L\_90t}$+θ$_{ref\_90}$)' is an out-phase reference signal having a phase difference of 90°. In this instance, the out-phase reference signal is synchronous with the response signal. A following signal is generated by synchronizing the response signal and the reference signal through a multiplier.

$$V_{PSD} = |Vsig||V_{L\_90}|\sin(\omega rt + \theta sig)\cos(\omega L\_90 t + \theta_{ref\_90}) =$$
$$1/2|Vsig||V_{L\_90}|\{\sin([\omega r - \omega_{L\_90}]t + \theta sig - \theta_{ref\_90}) -$$
$$\sin([\omega r + \omega_{L\_90}]t + \theta sig + \theta_{ref\_90})\}$$

The V$_{PSD}$(Phase Sensitive Detection) is a signal generated by synchronizing a reference signal(V$_L$) and a response signal(Vsig) through a multiplier. In this instance, when the signal passes through a low-pass filter (LPF), the AC component of the signal is removed. Accordingly, V$_{PSD}$ is '0'. However, when frequencies of the reference signal and the response signal are identical, i.e. ωr=ω$_{L\_90}$, an output of the LPF is 'Vout_90=½|Vsig||V$_{L\_90}$|sin(θsig−θ$_{ref\_90}$)'. Also, when '|Vsig||V$_L$|' is the same as 'Vout' and 'θsig−θref' is the same as 'θout', 'V$_{PSD\_filtered\_0}$' is the same as '½Voutcos(θout)'.

The signal is a conductivity signal in which the constant voltage signal is confirmed and the current is measured. Accordingly, the admittance is measured. FIG. 4 illustrates a graph of the admittance. In this instance, in FIG. 4, G designates a conductance, and B designates a susceptance. When G and an in-phase synchronous signal are combined, G may be measured. When B and a quadrature-phase synchronous signal are combined, B may be measured.

In this instance, to measure only the skin moisture content, a conductance component which reflects an effect of a sweat gland of the stratum corneum is required to be removed. Accordingly, only the susceptance may be measured by using the out-phase synchronous signal. According to the present embodiment, a method of measuring the skin moisture content may be applied by measuring the susceptance which varies over time. Specifically, the measurement module 100 may measure the susceptance which varies over time by the method described above that referred to FIGS. 2 through 4.

A differential rate calculation module 120 calculates a differential rate of skin impedance of a predetermined skin area which is measured for a predetermined period of time. For example, the predetermined period of time may correspond to a value between approximately 1 second and approximately 4 seconds. In this instance, the differential rate calculation module 120 may calculate the differential rate of the skin impedance which is measured between approximately 1 second and approximately 4 seconds immediately after a user starts measuring the skin impedance through the measurement module 110. The predetermined period of time may correspond to the value between approximately 1 second and approximately 4 seconds, or another value greater than approximately 4 seconds. In this instance, the predetermined period of time is required to be set as the value greater than approximately 1 second.

The calculating the differential rate of the skin impedance through the differential rate calculation module 120 is based on a principle in which the differential rate of a dry area and the differential rate of a moist area are different. Generally, skin moisture content for each anatomical area is different. Specifically, it may be proven that a distribution of the skin moisture content for each anatomical area is different through a predetermined experiment.

Figure 5:
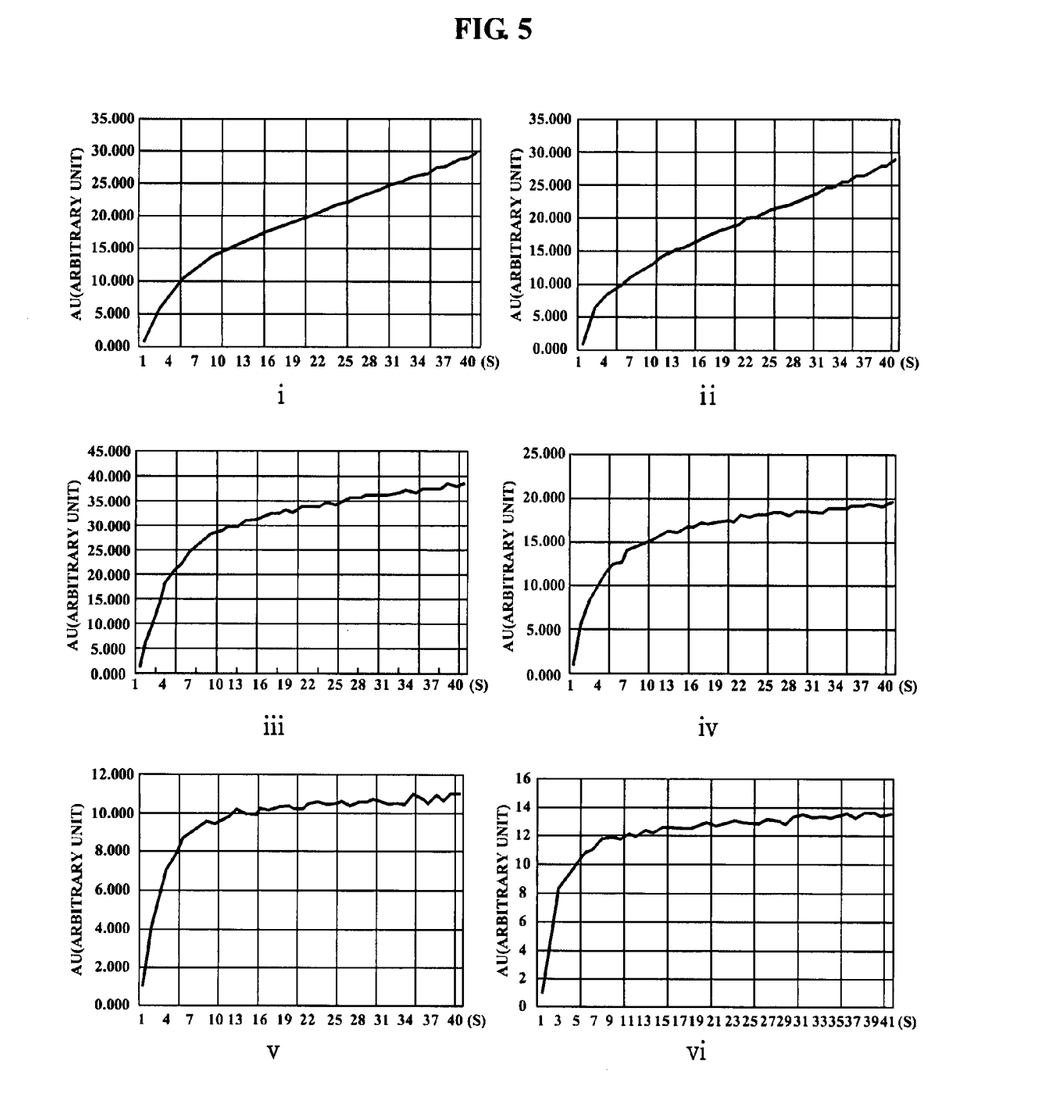
FIG. 5, parts (i), (ii), (iii), (iv), (v) and (vi), are graphs illustrating experimental results of a method of measuring skin moisture content by using a single low frequency according to an embodiment of the present invention.

FIG. 5, parts (i), (ii), (iii), (iv), (v) and (vi), are graphs illustrating experimental results of a method of measuring skin moisture content by using a single low frequency according to an embodiment.

Part (i) of FIG. 5 is a graph illustrating an experimental result of measuring skin moisture content from a forehead of a user. Part (ii) of FIG. 5 is a graph illustrating an experimental result of measuring skin moisture content from a cheek of the user. Part (iii) of FIG. 5 is a graph illustrating an experimental result of measuring skin moisture content from a palm of the user. Part (iv) of FIG. 5 is a graph illustrating an experimental result of measuring skin moisture content from a back of a hand of the user. Part (v) of FIG. 5 is a graph illustrating an experimental result of measuring skin moisture content from an outer arm of the user. Part (vi) of FIG. 5 is a graph illustrating an experimental result of measuring skin moisture content for an inner arm of the user. In FIG. 5, a vertical axis indicates an arbitrary unit (AU) within a range from 0 to 130, and a horizontal axis indicates seconds.

A protocol of the experiment according to an embodiment, which derives the graphs of FIG. 5 parts (i) through (vi), may be applied by referring to a variety of conventional references with respect to measuring skin moisture content. To maintain a steady temperature and moistness, the experimental laboratory always maintained a constant temperature (20±2° C.) and a constant moistness (50±5%). Also, the experimental environment described above was maintained for at least 30 minutes before the experiments started. There were 24 subjects for the experiment. Also, the subjects were required to not wash an area to be measured and not put on any makeup for at least 12 hours before the experiment started. The subjects were also required to be sterilized by alcohol upon arrival at the laboratory, and be exposed to air for 30 minutes after sterilization. The measurements were made in an order of the forehead, the cheek, the outer arm, the back of the hand, the inner arm, and the palm, for approximately 4 seconds, respectively. Also, each measurement was repeated 5 times at intervals of approximately 5 seconds between each measurement. In the experiment, the age distribution of male subjects was 34.5±2.73 years old, the age distribution of female subjects was 24.4±1.33 years old, and the age distribution of all the subjects was 26.08±2.46 years old.

As a result of the experiment, as shown in FIG. 5 parts (i) through (vi), the graphs of the forehead, the cheek, and the palm, which are known as moist areas, are different from the graphs of the outer arm, the inner arm, and the back of the hand, which are known as the dry areas. Specifically, as shown in FIG. 5 parts (i) through (vi), the differential rate of up to approximately 1 second in the moist area is similar to the differential rate of up to approximately 1 second in the dry area. However, the differential rate in the moist area is gradually increased, unlike the differential rate in the dry area after approximately 1 second elapses. Also, the differential rate in the dry area showed a tendency towards saturation.

The apparatus to measure skin moisture content 100 according to an embodiment may automatically determine whether the skin area is a moist area or a dry area by measuring a difference of the differential rate of the susceptance, i.e. the skin moisture content for each skin area, for a predetermined period of time. Specifically, whether the skin area is a moist area or a dry area is determined based on a principle in which the differential rate in the moist area is gradually increased after approximately 1 second elapses and the differential rate in the dry area shows a tendency toward saturation.

When the differential rate calculation module 120 calculates the differential rate of the skin impedance which is measured approximately 1 second after an initial measurement, the skin state determination module 130 compares the calculated differential rate with a predetermined threshold.

The threshold may be set by the experiment described through FIG. 5. However, in this specification, as an example of the threshold, a differential rate of 0.18, which is derived from the experiment, is used. The threshold may be set differently depending upon a skin characteristic of a user.

As a result of comparing the calculated differential rate and the threshold, when the differential rate is greater than or equal to the threshold, the skin state determination module 130 determines that the skin area is a moist area. Also, as a result of the comparison, when the differential rate is less than the threshold, the skin state determination module 130 determines that the skin area is a dry area.

The skin state determination module 130 determines a state of skin moisture of the skin area by referring to a skin moisture content table according to a result of the comparison. The memory device 140 maintains the skin moisture content table.

Figure 6:
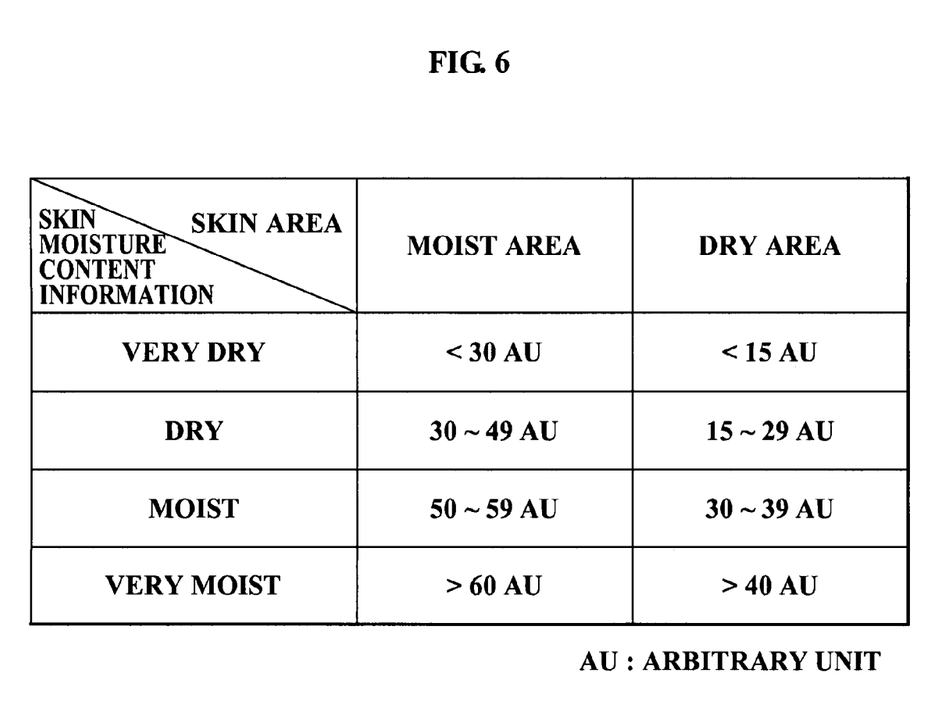
FIG. 6 is a table illustrating a skin moisture content table according to an embodiment of the present invention.

FIG. 6 a table illustrating a skin moisture content table according to the embodiment.

As shown in FIG. 6, the skin moisture content table may store a skin impedance value of each skin area which is classified into a moist area and a dry area, and skin moisture content information corresponding to the skin impedance value. As illustrated in FIG. 6, a unit of the skin impedance value may be set to an arbitrary unit (AU) within a range from 0 to 130. A skin state determination module 130 may determine a skin state of the skin area by referring to the skin moisture content table.

For example, when the skin area is determined to be a moist area, and the measured skin impedance value is 35, the skin state determination module 130 may determine that the skin area is a dry area. Also, when the skin area is determined to be a dry area, and the measured skin impedance value is 35, the skin state determination module 130 may determine that the skin area is a moist area. As described above, although the measured skin impedance values are identical, the skin state determination module 130 may differently determine a current skin state depending upon the skin state of the skin area.

A memory device 140 may include a memory in order to store the skin moisture content table. In this instance, the memory includes a Universal Serial Bus (USB) memory, a Compact Flash (CF) memory, a Secure Digital (SD) memory, a mini SD memory, a XD memory, a memory stick, a memory stick duo, a Smart Media Card (SMC) memory, a Multi Media Card (MMC) memory, or a Reduced Sized-MMC (RS-MMC) memory. Also, the memory device 140 may include a hard disk which is used in a general personal computer (PC) or a notebook PC. Also, the memory device 140 may be embedded in the apparatus to measure skin moisture content 100 or may be an external memory device.

An output device 150 may display skin moisture content information to the user. Specifically, the output device 150 may display information as to whether the skin area is a moist area or a dry area, which is determined by the skin state determination module 130, and information on the current skin state. The output device 150 may display the information on a predetermined display device, or replay the information through an audio output device such as a speaker.

A user interface module 160 receives information about the skin area where the user wants to measure the skin moisture content. Specifically, when the skin area of the user does not have the differential rates of the skin impedance values in the moist area and the dry area, as described through the experiment described with reference to FIG. 5, the user interface module 160 may measure the skin moisture content of the skin area, after the user inputs the information of the skin area, which is a moist area, such as the forehead or the cheek, or a dry area, such as the back of the hand or the inner arm.

As described above, the apparatus to measure skin moisture content 100 according to an embodiment may provide an automatic mode to a user having a skin characteristic like an experimental result described with reference to FIG. 5, and a manual measurement mode to a user having another skin characteristic. In this instance, previously inputting the information of the skin area to be measured is not needed in the automatic mode. Conversely, when measuring the skin moisture content, previously inputting the information of the skin area to be measured is needed in the manual mode.

As described above, when determining whether the user is the user for the automatic mode or the user for the manual mode, a predetermined calibration procedure described above is previously needed.

Specifically, when the user initially measures the skin moisture content through the apparatus to measure skin moisture content 100, the user is required to measure the skin moisture content for each of the skin areas, and the differential rate of the skin impedance which is measured for each of the skin areas may be compared.

In this instance, when the user has the skin characteristic in which the differential rate of the skin impedance value, after approximately 1 second elapses after measuring skin impedance in the moist area, is greater than a threshold, and the skin characteristic of the user is that the differential rate of the skin impedance value, after approximately 1 second elapses after measuring in the dry area, is less than the threshold, the user may be confirmed to be a user using the automatic mode. In this instance, the automatic mode may be applied to the method of measuring skin moisture content according to an embodiment. Accordingly, whether the skin area of the user in the automatic mode is the moist area or the dry area may be automatically determined by the apparatus to measure skin moisture content 100 after the calibration procedure, without separately inputting the information of the skin area to be measured.

However, as a result of the calibration procedure, when the user has a skin characteristic in which the differential rate of the skin impedance value after approximately 1 second of measuring both the moist area and the dry area is less than the threshold, the apparatus to measure skin moisture content 100 requests the user to input the information of the skin area to be measured. Accordingly, the apparatus to measure skin moisture content 100 according to an embodiment may provide all users accurate skin moisture content information. Also, when the user is the user in the manual mode, and has the skin characteristic described above in which the differential rate of the skin impedance value is different for each of the skin areas, the differential rate of the skin impedance which is repeatedly measured in the same area is similar. Accordingly, the automatic mode for the user may be set by establishing a determination standard using data only for the user.

The automatic mode, the manual mode, and a calibration method will be described in detail by referring to FIGS. 7 through 9.

Figure 7:
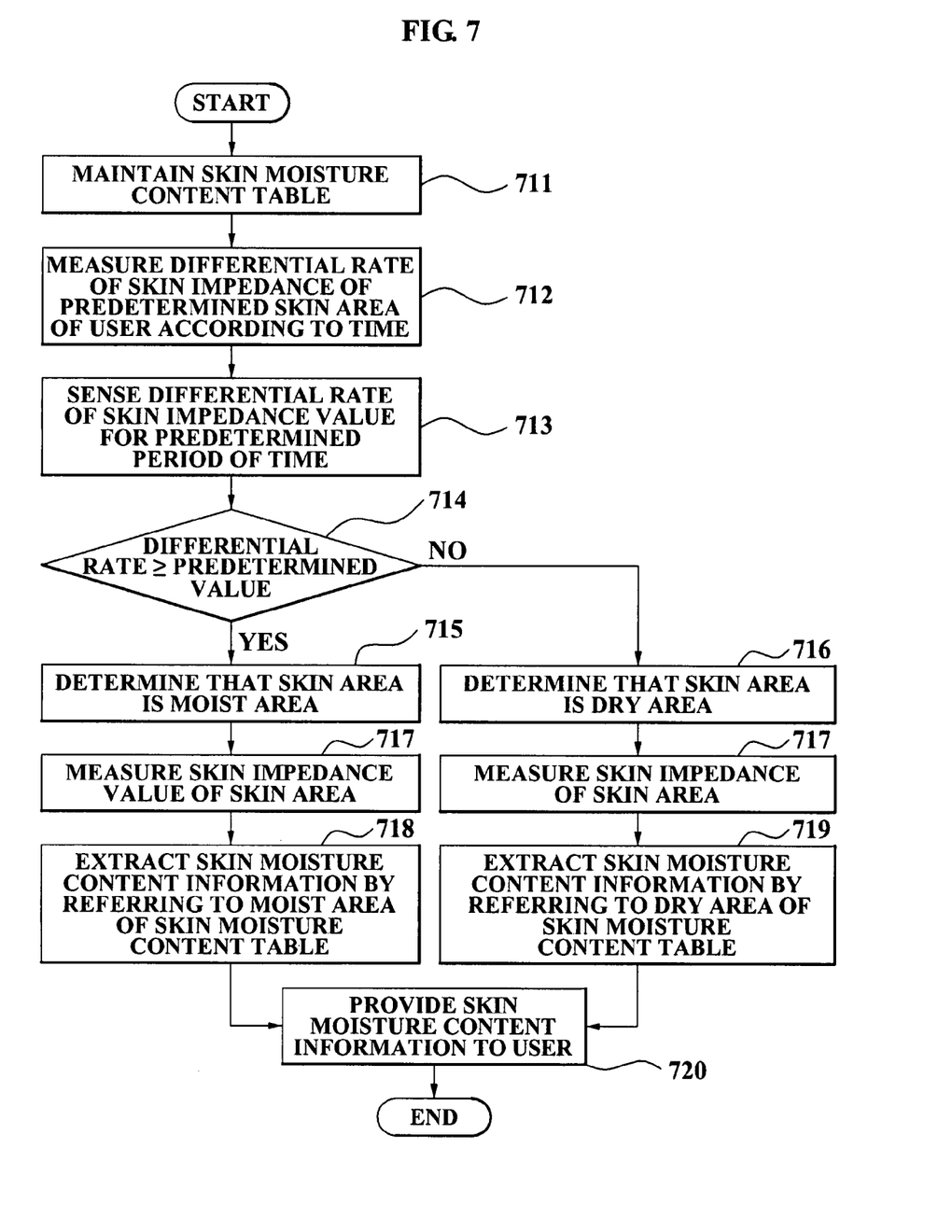
FIG. 7 is a flowchart illustrating a method of measuring skin moisture content when a measurement mode is an automatic mode according to an embodiment of the present invention.

FIG. 7 is a flowchart illustrating a method of measuring skin moisture content when a measurement mode is an automatic mode according to an embodiment.

In operation 711, an apparatus to measure skin moisture content according to an embodiment maintains a skin moisture content table which stores a skin impedance value for each of the skin areas which are classified into at least two skin areas, i.e., a moist area and a dry area, and skin moisture content information corresponding to the skin impedance value.

In operation 712, the apparatus to measure skin moisture content measures a differential rate of the skin impedance of a predetermined skin area of a user for a predetermined period of time. In operation 713, the apparatus to measure skin moisture content senses the differential rate of the skin impedance value for a predetermined period of time. In this instance, the predetermined period of time may correspond to a value between approximately 1 second and approximately 4 seconds, for example.

When the differential rate is greater than or equal to a predetermined value for the predetermined period of time in operation 714, the apparatus to measure skin moisture content determines that the skin area is a moist area in operation 715. Also, when the differential rate is less than the predetermined value for the predetermined period of time in operation 714, the apparatus to measure skin moisture content determines that the skin area is a dry area in operation 716. In this instance, the predetermined value may be variously set.

In operation 717, when the skin area is determined to be a moist area or a dry area, the apparatus to measure skin moisture content measures the skin impedance of the skin area.

In operation 718, when the skin area is a moist area, the apparatus to measure skin moisture content extracts skin moisture content information of the skin area by referring to the moist area of the skin moisture content table. Also, in operation 719, when the skin area is a dry area, the apparatus to measure skin moisture content extracts the skin moisture content information of the skin area by referring to the dry area of the skin moisture content table. In operation 720, the apparatus to measure skin moisture content may provide the skin moisture content information to the user by displaying the extracted skin moisture content information on a predetermined display device, or replaying the skin moisture content information through a predetermined audio output device.

Figure 8:
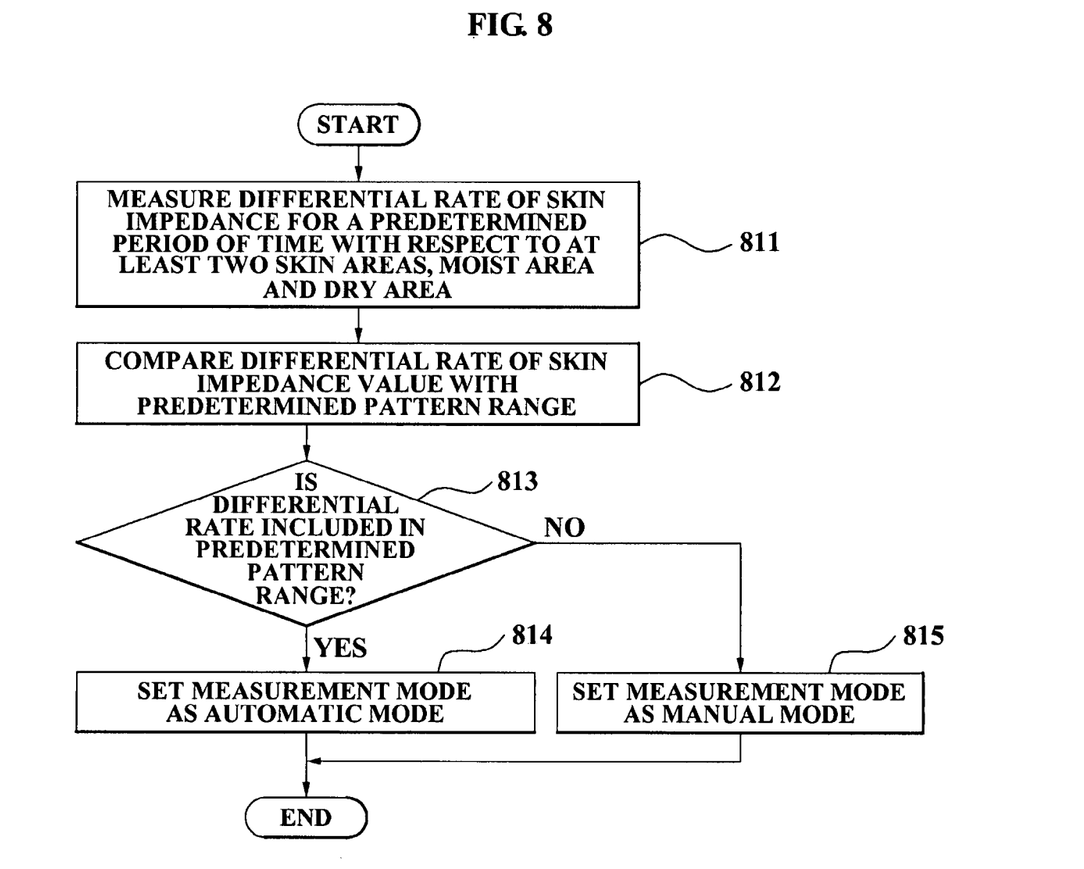
FIG. 8 is a flowchart illustrating a calibration method when a user initially measures skin moisture content through an apparatus to measure skin moisture content according to an embodiment of the present invention.

FIG. 8 is a flowchart illustrating a calibration method when a user initially measures skin moisture content through an apparatus to measure skin moisture content according to an embodiment.

In operation 811, an apparatus to measure skin moisture content according to an embodiment measures a differential rate of a skin impedance according to a time, with respect to at least two skin areas, i.e., a moist area and a dry area.

Specifically, when the user initially measures the skin moisture content through the apparatus to measure skin moisture content, user information is not stored in the apparatus to measure skin moisture content. In this instance, the user information includes information on whether the user is a user in an automatic mode or a user in a manual mode. Also, the apparatus to measure skin moisture content may measure the differential rate of the skin impedance of the skin area for a predetermined period of time. The skin area may be set to include at least one of the moist area, such as a forehead and a cheek, and the dry area, such as a back of a hand and an outer arm, respectively.

In operation 812, the apparatus to measure skin moisture content compares the differential rate of the skin impedance value with a predetermined pattern range. The predetermined pattern range may be set by a graph of the skin impedance value for each of the skin areas, which is described in FIG. 5. Specifically, the differential rate in the moist area gradually increases after approximately 1 second, and the differential rate in the dry area shows a tendency toward saturation.

In operation 813, when the differential rate is determined to be included in the predetermined pattern range, the apparatus to measure skin moisture content determines that the user is a user in the automatic mode, and may store information of the skin area of the user in a predetermined memory device 140. In operation 814, the apparatus to measure skin moisture content then sets a measurement mode as the automatic mode.

In operation 813, when the differential rate is determined not to be included in the predetermined pattern range, the apparatus to measure skin moisture content determines that the user is a user in the manual mode, and may store information of the skin area of the user in a predetermined memory device 140. In operation 815, the apparatus to measure skin moisture content sets the measurement mode as the manual mode after receiving the information of the skin area of the user.

Figure 9:
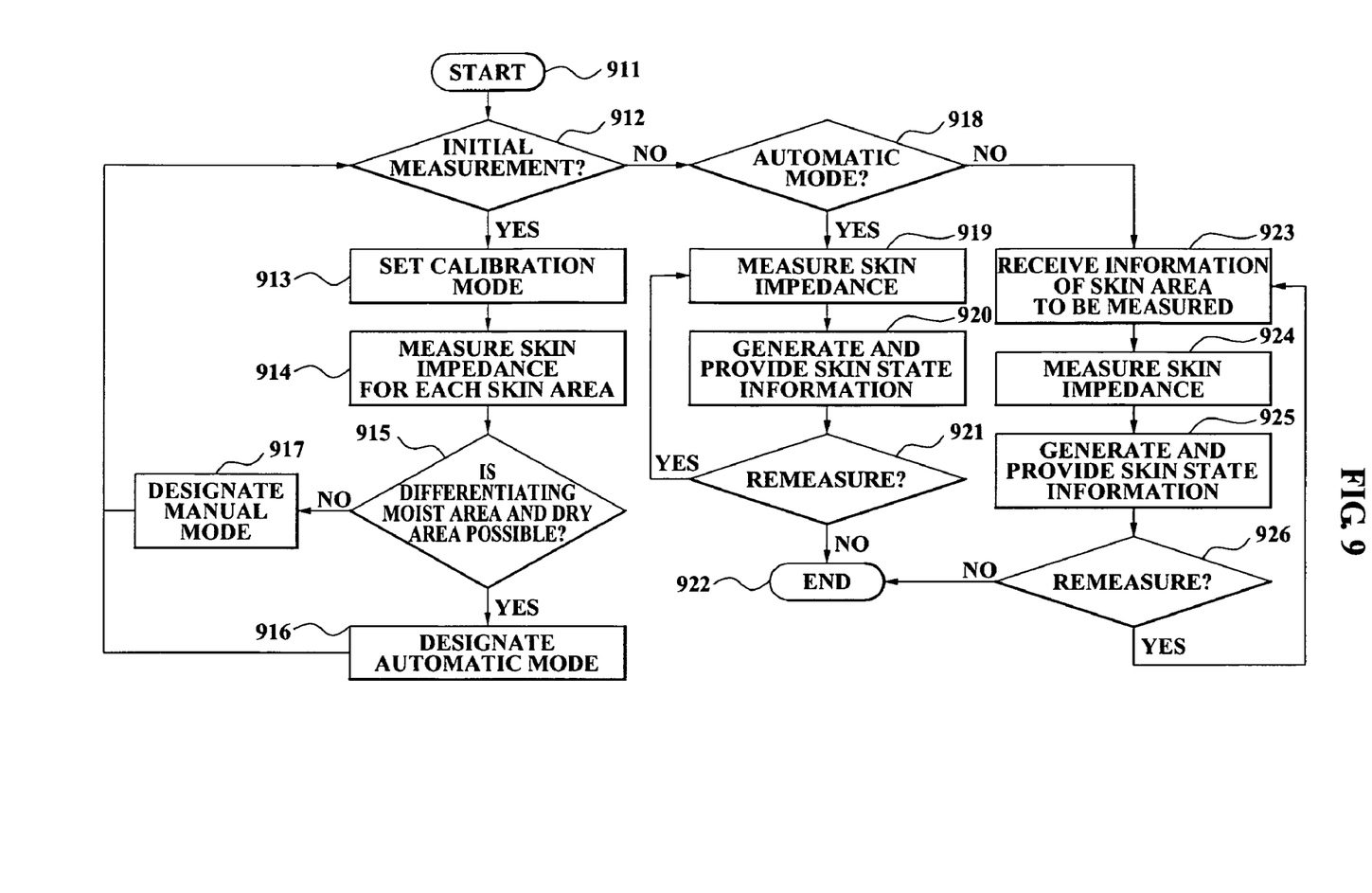
FIG. 9 is a flowchart illustrating a method of measuring skin moisture content according to an embodiment of the present invention.

FIG. 9 is a flowchart illustrating a method of measuring skin moisture content according to an embodiment.

When an apparatus to measure skin moisture content according to an embodiment receives a request to measure the skin moisture content and starts to measure the skin moisture content in operation 911, the apparatus to measure skin moisture content determines whether a skin moisture content measurement of a user is an initial measurement in operation 912. When the skin moisture content measurement of the user is the initial measurement in operation 912, the apparatus to measure skin moisture content sets a calibration mode in operation 913.

In operation 914, the apparatus measures the skin impedance for each skin area, and compares the differential rate of the skin impedance with a threshold. In operation 915, the apparatus determines whether differentiating the differential rate of the skin impedance in the moist area and the differential rate of the skin impedance value in the dry area is possible.

In this instance, when differentiating is possible in operation 915, the apparatus designates the automatic mode as a default mode in operation 916. However, when the differentiating is not possible in operation 915, the apparatus designates the manual mode as the default mode in operation 917.

In operation 912, when the skin moisture content measurement of the user is not the initial measurement, the apparatus determines whether the default mode is the automatic mode in operation 918. When the default mode is determined to be the automatic mode in operation 918, the apparatus measures the skin impedance of the skin area which the user desires to measure in operation 919.

In operation 920, the apparatus determines whether the skin area is a moist area or a dry area through the measured skin impedance, and generates and provides skin state information of the skin area, as a result of the determination. When the apparatus receives a request for a remeasurement from the user in operation 921, the apparatus returns to operation 919. However, when the apparatus does not receive the request for the remeasurement from the user in operation 921, the apparatus to measure skin moisture content ends operations of measuring the skin moisture content in operation 922.

When the default mode is not the automatic mode, and thus is the manual mode in operation 918, the apparatus receives the information of the skin area which the user desires to measure in operation 923. When the user measures the skin impedance of the skin area in operation 924, the apparatus generates and provides the skin state information of the skin area in operation 925. When the apparatus receives the request for a remeasurement from the user in operation 926, the apparatus returns to operation 923. However, when the apparatus to measure skin moisture content does not receive the request for the remeasurement from the user in operation 926, the apparatus ends operations of measuring the skin moisture content in operation 922.

The method of measuring the skin moisture content which has been described in FIGS. 7 through 9 may be embodied including a configuration and operations of the apparatus to measure skin moisture content which has been described in FIGS. 1 through 5.

The method of measuring the skin moisture content according to the above-described embodiment may be recorded in computer-readable media including program instructions to implement various operations embodied by a computer. The media may also include, alone or in combination with the program instructions, data files, data structures, etc. The media and program instructions may be those specially designed and constructed for the purposes of the present invention, or they may be of the kind well-known and available to those having skill in the computer software arts. Examples of computer-readable media include magnetic media, such as hard disks, floppy disks, and magnetic tape; optical media, such as CD ROM disks and DVD; magneto-optical media, such as optical disks; and hardware devices that are specially configured to store and perform program instructions, such as read-only memory (ROM), random access memory (RAM), flash memory, and the like. The media may also be a transmission medium, such as optical or metallic lines, wave guides, etc. including a carrier wave transmitting signals specifying the program instructions, data structures, etc. Examples of program instructions include both machine code, such as produced by a compiler, and files containing higher level code that may be executed by the computer using an interpreter. The described hardware devices may be configured to act as one or more software modules in order to perform the operations of the above-described embodiments of the present invention.

The apparatus to measure skin moisture content and a method of operating the same according to the above-described embodiments measures a differential rate of a skin impedance of a predetermined skin area of a user for a predetermined period of time, determines whether the skin area of the user is a moist area or a dry area, and may more easily measure the skin moisture content without separately inputting information of the skin area or referring to a particular table.

Also, the apparatus to measure skin moisture content and a method of operating the same according to the above-described embodiments, allows a user to initially measure a skin moisture content through the apparatus to measure the skin moisture content, which performs a calibration procedure considering a differential rate of a skin impedance value which is measured in a moist area for a predetermined period of time, determines whether a measurement mode is an automatic mode or a manual mode of measuring the skin impedance, and thereby may optimally measure the skin moisture content according to a skin characteristic of the user.

Although a few embodiments have been shown and described, it would be appreciated by those skilled in the art that changes may be made to these embodiments without departing from the principles and spirit of the invention, the scope of which is defined by the claims and their equivalents.

What is claimed is:

1. An apparatus measuring skin moisture content, the apparatus comprising:
   a memory device maintaining a skin moisture content table which stores a skin impedance value of each of a plurality of skin areas, each of the skin areas being classified into at least a moist area and a dry area prior to measuring skin impedance of a predetermined skin area of a user, and skin moisture content information corresponding to the skin impedance value;
   a measurement module measuring the skin impedance of the predetermined skin area of the user;
   a differential rate calculation module measuring a differential rate of skin impedance at a same position of the predetermined skin area for a predetermined period of time,
   wherein the differential rate calculation module continuously calculates the differential rate of the skin impedance for a predetermined period of time;
   a skin state determination module determining that the skin area is the moist area when the differential rate is greater than or equal to a predetermined value of the stored skin impedance value for the predetermined skin area for a predetermined period of time, determining that the skin area is the dry area when the differential rate is less than the predetermined value of the stored skin impedance value for the predetermined skin area for the predetermined period of time, and extracting the skin moisture content information which corresponds to the measured skin impedance value by referring to the skin moisture content table; and
   an output device providing the skin moisture content information to the user.

2. The apparatus of claim 1, wherein the predetermined period of time corresponds to a value between 1 second and 4 seconds from immediately after initial measuring of the differential rate of skin impedance.

3. An apparatus to measure skin moisture content, the apparatus comprising:
   a measurement module measuring skin impedance of a predetermined skin area of a user;
   a differential rate calculation module measuring a differential rate of skin impedance at a same position of the predetermined skin area for a predetermined period of time,
   wherein the differential rate calculation module continuously calculates the differential rate of the skin impedance for a predetermined period of time;
   a skin state determination module determining that the skin area is a moist area when the differential rate is greater than or equal to a predetermined value for a predetermined period of time and determining that the skin area is a dry area when the differential rate is less than the predetermined value for the predetermined period of time; and
   an output device providing skin moisture content information corresponding to the skin area being the moist area or the dry area to the user.

4. The apparatus according to claim 3, wherein after the skin area is determined to be one of the dry area or the moist area, a skin state of the skin area is determined based on whether the skin area is determined to be a dry area or a moist area and a corresponding skin moisture content table.

* * * * *